United States Patent
Konya et al.

[11] Patent Number: 5,342,547
[45] Date of Patent: Aug. 30, 1994

[54] AGENTS FOR CONTROLLING UNDERWATER FOULING ORGANISMS

[75] Inventors: Kazumi Konya; Nobuyoshi Shimizu; Wataru Miki, all of Shimizu, Japan

[73] Assignee: Marine Biotechnology Institute Co., Ltd., Tokyo, Japan

[21] Appl. No.: 3,593

[22] Filed: Jan. 13, 1993

[30] Foreign Application Priority Data

Jan. 14, 1992 [JP] Japan ................. 4-005065
Nov. 16, 1992 [JP] Japan ................. 4-305519

[51] Int. Cl.$^5$ .............................. C09D 5/14
[52] U.S. Cl. ..................... 252/380; 106/18.32; 106/16; 210/749; 210/764; 422/1; 422/6; 424/538; 523/122
[58] Field of Search ............ 424/538; 208/48 AA; 252/380, 1; 210/749, 764; 422/1, 6; 523/122; 106/18.32, 16

[56] References Cited

U.S. PATENT DOCUMENTS

4,443,615 4/1984 Matsuoka et al. ............ 548/489
4,778,653 10/1988 Kamimura et al. ............ 422/6
4,933,011 6/1990 Rei ..................... 106/18.32

FOREIGN PATENT DOCUMENTS

54-122729 3/1978 Japan .
55019223 7/1978 Japan .
WO80/06975 6/1990 PCT Int'l Appl. .

OTHER PUBLICATIONS

A. Sato and W. Fenical, "Gramine–Derived Bromo–Alkaloids From the Marine Bryozoan *Zoobotryon Verticillatum*," Tetrahedron Letters, vol. 24, No. 5, pp. 481–484 (1983).

*Primary Examiner*—Robert L. Stoll
*Assistant Examiner*—Valerie Fee
*Attorney, Agent, or Firm*—Limbach & Limbach

[57] ABSTRACT

The present invention relates to an underwater antifouling composition which contains at least one indole compound represented by the Formula (1) which serves as an underwater anti-fouling agent:

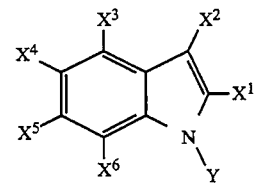

wherein Y is selected from the group consisting of hydrogen, lower alkyl and phenyl; and wherein $X^1$, $X^2$, $X^3$, $X^4$, $X^5$ and $X^6$ are independently selected from the group consisting of hydrogen, halogen, lower alkyl, lower alkoxy, nitro, cyano, cyano lower alkyl, halogenated lower alkyl, substituted or unsubstituted phenyl, aralkyl, aralkyloxy, lower alkoxycarbonyl, aliphatic lower acyl, aliphatic lower acyloxy, lower alkoxycarbonyl-lower alkyl, aromatic acyl, lower-cycloalkylamino-lower alkyl, nitrovinyl, pyridyl lower alkyl, carbamoyl lower alkyl, carbamoyl, diallylamino lower alkyl and di-lower-alkylamino-lower alkyl.

The present invention also relates to a method for preventing the accumulation of underwater fouling organisms on a surface by treating the surface with the underwater anti-fouling composition of the present invention.

9 Claims, No Drawings

AGENTS FOR CONTROLLING UNDERWATER FOULING ORGANISMS

RELATED APPLICATIONS

This application claims foreign priority based on Japanese Patent Application No. 305519/1992 filed Nov. 16, 1992 and Japanese Patent Application No. 5065/1992 filed Jan. 14, 1992.

INTRODUCTION

The present invention relates to agents that prevent unwanted fouling organisms from attaching and growing on ship hulls, culturing nets, set-nets, sea equipment such as buoys, the cooling water tubes of atomic power plants or thermal electric power plants, and the inlet channels of heat exchangers in the petrochemical industry.

BACKGROUND OF THE INVENTION

In ship hulls, underwater structures, the inlet channels of a cooling water tubes and other structures that are always exposed to water, there are various shellfish and algae such as *Balanus, Mytilus, Hydroza, Ulva, Enteromorpha* as well as others that attach and grow, or even overgrow. The attachment of these organisms to these structures causes economic damage in various forms: increased attachment to ship hulls slows down the cruising speed of these vessels, increases fuel consumption and also causes serious economical loss due to the cancellation of service in order to clean the ship hulls. Their attachment to cooling water equipment decreases heat conductivity which eventually reduces the cooling power of the equipment.

A variety of agents useful for controlling fouling organisms in fresh water or sea water have been used to prevent the attachment and overgrowth of these organisms. Copper compounds and organotin compounds are known active anti-fouling agents, and are still extensively used today. Anti-fouling agents in the form of a paint can contain 10–50% by weight of the active ingredient and can be used to paint surfaces such as ship hulls. The paint prevents attachment and growth of fouling organisms by continuously releasing anti-fouling agents underwater.

SUMMARY OF THE INVENTION

The reagents of the present invention have excellent anti-fouling properties against underwater fouling organisms. The reagents are more effective than conventional anti-fouling agents containing heavy metals and, more importantly, are safe for our health and the environment.

DETAILED DESCRIPTION OF THE INVENTION

Environmental problems such as polluted rivers and sea with heavy metals and toxic compounds have been caused by the industrial use of such materials. For example, stern warnings have been issued regarding the effects of heavy metal compounds, especially organotin compounds which are widely used and known to be effective anti-fouling reagents because of their effect on the natural environment and on our health when accumulated in our body via food such as fish and shellfish. Therefore, there is a need for the development of safe and effective anti-fouling compounds.

The present inventors have attempted to develop highly-safe, and effective anti-fouling compounds. It has been found that particular indole compounds have an excellent repellent effect against fouling organisms.

The present invention provides anti-fouling reagents comprising, as active ingredients, indole compounds represented by Formula (1):

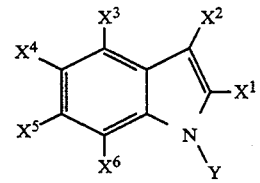

(wherein Y represents hydrogen, lower alkyl, or phenyl; $X^1$, $X^2$, $X^3$, $X^4$, $X^5$ and $X^6$ independently represent hydrogen, halogen, lower alkyl, lower alkoxy, nitro, cyano, cyano lower alkyl, halogenated lower alkyl, substituted or unsubstituted phenyl, aralkyl, aralkyloxy, lower alkoxycarbonyl, aliphatic lower acyl, aliphatic lower acyloxy, lower-alkoxycarbonyl-lower alkyl, aromatic acyl, lower-cycloalkylamino-lower alkyl, nitrovinyl, pyridyl lower alkyl, carbamoyl lower alkyl, carbamoyl, diallylamino lower alkyl or di-lower-alkylamino-lower alkyl).

In Formula (1), lower alkyl represented by $X^1$, $X^2$, $X^3$, $X^4$, $X^5$, $X^6$ or Y refers to a straight or branched alkyl group having 1–5 carbon atoms and includes methyl, ethyl, propyl, isopropyl, sec-butyl, tert-butyl, pentyl and hexyl. Examples of halogen represented by $X^1$, $X^2$, $X^3$, $X^4$, $X^5$ and $X^6$ includes a fluorine, chlorine, bromine or iodine atom. Lower alkoxy refers to alkoxy groups having 1–5 carbon atoms and includes methoxy, ethoxy, propoxy and butoxy. Cyano lower alkyl refers to said lower alkyl substituted by a cyano group. Examples of cyano lower alkyl includes a cyanomethyl, cyanoethyl and cyanopropyl group. Halogenated lower alkyl refers to said lower alkyl substituted by said halogen. Examples of halogenated lower alkyl includes a chloromethyl, trifluoromethyl and 2-bromoethyl group. Examples of substituted phenyl includes a phenyl group substituted by amino group, said halogen, said lower alkyl or said lower alkoxy. Examples of aralkyl include a benzyl group. Examples of aralkyloxy include a benzyloxy group. Lower alkoxycarbonyl refers to carbonyls having 2–6 carbon atoms and includes methoxycarbonyl, ethoxycarbonyl, propoxycarbonyl, butoxycarbonyl. Aliphatic lower acyl refers to compounds having 2–6 carbon atoms and includes acetoxy and propionyloxy. Lower-alkoxycarbonyl-lower alkyl refers to said lower alkyl substituted by said lower alkoxycarbonyl and lower-alkoxycarbonyl-lower alkyl includes methoxycarbonylmethyl and ethoxycarbonylethyl. Examples of an aromatic acyl include unsubstituted benzoyl or a benzoyl group substituted by amino, said halogen, said loweralkyl, or said lower alkoxy; Lower-cycloalkylamino-lower alkyl means said lower alkyl substituted by lower cycloalkylamino having 3–7 carbon atoms. Examples of lower-cycloalkyamino-lower alkyl include cyclohexylaminomethyl, cyclohexylaminoethyl, cyclopentylaminomethyl and cyclopentylaminoethyl. Pyrdyl lower alkyl refers to said lower alkyl substituted by pyridyl and examples of pyridyl lower alkyl includes pyridylmethyl, pyridylethyl, and pyridylpropyl. Carbamoyl lower alkyl refers to said lower alkyl substituted by carbamoyl and examples of carbamoyl lower alkyl includes carbamoylmethyl carbamoylethyl and carbamoylpropyl. Diallylamino-lower alkyl refers to said lower alkyl includes diallylaminomethyl, diallylaminoethyl and diallylaminopropyl. Di-lower-alkylamino-lower alkyl means said lower alkyl substituted by did-lower-alkylamino and examples of di-lower-alkylamino-lower alkyl includes dimethylaminomethyl, dimethylaminoethyl and dimethylaminopropyl.

Examples of indole compounds represented by Formula (1) include but are not limited to those compounds listed in Table 1.

TABLE 1

| Compound No. | Chemical name |
| --- | --- |
| 1 | 2,3-Dimethylindole |
| 2 | 3-Indolylacetronitrile |
| 3 | 3-Indolylacetate |
| 4 | Ethyl 5-chloro-2-indolecarboxylate |
| 5 | 1-Methylindole |
| 6 | 5-Methylindole |
| 7 | 3-(2-Nitrovinyl)-1-phenylindole |
| 8 | 4-Chloroindole |
| 8 | 6-Chloroindole |
| 10 | 5,6-Dimethoxyindole |
| 11 | 4-Methoxyindole |
| 12 | 4-Methylindole |
| 13 | 6-Methylindole |
| 14 | 4-Indolylacetate |
| 15 | 4-Nitroindole |
| 16 | Methyl 4-indolecarboxylate |
| 17 | Ethyl 3-indoleacetate |
| 18 | 3-Indolylacetamide |
| 19 | 4-Methoxy-1-methylindole |
| 20 | 3-Cyanoindole |
| 21 | 1,2-Diphenylindole |
| 22 | Methyl 4-methoxy-2-indolecarboxylate |
| 23 | Methyl 6-methoxy-2-indolecarboxylate |
| 24 | Methyl 4,6-dimethoxy-2-indolecarboxylate |
| 25 | Dimethyl 2,3-indoledicarboxylate |
| 26 | 3-(2-Bromoethyl) indole |
| 27 | 3-Acetylindole |
| 28 | 5-Benzyloxyindole |
| 29 | 5-Bromoindole |
| 30 | 5-Chloroindole |
| 31 | 5-Chloro-2-methylindole |
| 32 | 5-Cyanoindole |
| 33 | 1,2-Dimethylindole |
| 34 | 2,5-Dimethylindole |
| 35 | Ethyl 2-indolecarboxylate |
| 36 | 5-Fluoroindole |
| 37 | 5-Methoxyindole |
| 38 | 5-Methoxy-2-methylindole |
| 39 | 2-Methylindole |
| 40 | 3-Methylindole |
| 41 | 7-Methylindole |
| 42 | 5-Nitroindole |
| 43 | 6-Nitroindole |
| 44 | 2-Phenylindole |
| 45 | 5-Bromo-3-indolylacetate |
| 46 | 3-Carbamoyl-2-methylindole |
| 47 | 1-Ethyl-2-phenylindole |
| 48 | 1-Methyl-2-phenylindole |
| 49 | 1-Methyl-3-indolylacetate |
| 50 | 3-(Cyclohexylaminomethyl)indole |
| 51 | 2-Methyl-3-propionylindole |
| 52 | 5-Benzyloxy-3-indolylacetamide |
| 53 | 5-Benzyloxy-3-indolylacetonitrile |
| 54 | Ethyl 5-benzyloxy-2-indolecarboxylate |
| 55 | Ethyl 5-methyl-2-indolecarboxylate |
| 56 | 2-Methyl-3-propylindole |
| 57 | 3-Benzylindole |
| 58 | Methyl (3-(3-indolyl)propionate |
| 59 | 3-Propionylindole |
| 60 | 3-(3-Indolyl)propionitrile |
| 61 | 2,3-Dimethyl-5-nitroindole |
| 62 | 3-Diallylaminomethylindole |
| 63 | Methyl 3-indolylacetate |
| 64 | 3-(2-Nitrovinyl)indole |
| 65 | 3-[2-(3-Pyridyl)ethyl]indole |
| 66 | 3-Ethyl-2-methyl-5-nitroindole |

TABLE 1-continued

| Compound No. | Chemical name |
| --- | --- |
| 67 | 5-Chloro-2-phenylindole |
| 68 | 3-(4-Chlorobenzoyl)-2-methylindole |
| 69 | 2-(2-Aminophenyl)indole |
| 70 | Gramine |
| 71 | 1-Methylgramine |
| 72 | 2-Methylgramine |
| 73 | 5-Methylgramine |
| 74 | 6-Methylgramine |
| 75 | 5-Methoxygramine |
| 76 | 5-Fluorogramine |
| 77 | 6-Fluorogramine |
| 78 | 5-Bromogramine |
| 79 | 6-Bromogramine |
| 80 | 4-Chlorogramine |
| 81 | 5-Chlorogramine |
| 82 | 5-Benzyloxygramine |
| 83 | 6-Benzyloxygramine |
| 84 | 1,2-Dimethylgramine |
| 85 | 2,6-Dibromogramine |
| 86 | 5,6-Dibromogramine |
| 87 | 6-Bromo-2-methylgramine |
| 88 | 2,5,6-tribromogramine |
| 89 | 5,6-Dibromo-2-methylgramine |
| 90 | 2,6-Dibromo-1-methylgramine |
| 91 | 2,5,6-Tribromo-1-methylgramine |
| 92 | N,N-dimethyl-5-methoxytryptamine |
| 93 | N,N-dimethylhomotryptamine |

The indole compounds shown in Table 1 are all known compounds and can be chemically synthesized by conventional methods known in the art.

Most of the indole compounds described above are found in animals, plants and bacteria and can be obtained by extraction and purification from these organisms. For example, 2,5,6-Tribromo-1-methylgramine (Compound No. 91), an indole compound represented by the formula (1) wherein $X^1$, $X^4$ and $X^5$ are bromine; $X^3$ and $X^6$ are hydrogen; $X^2$ is dimethylaminomethyl; and Y is methyl, is known to be found in *Zoobotryon verticillatum*, a species of *Bryozoa* [Aiya Sato et al., *Tetrahedron Lett.*, 24, 481. (1983)]. In addition, Compound No. 91 can also be extracted and purified from *Zoobotryon pellucidum*, as is disclosed by the present inventors.

Solvents used for extracting these compounds include typical organic solvents, preferably acetone or ethanol. Purification methods include those known in the art such as partition chromatography, preferably silica gel chromatography using a mixture of hexane and ethyl acetate as an eluent.

The indole compounds used as the active ingredient in the present invention may be used alone or in combination with other anti-fouling agents. Active ingredients extracted from organisms may be used as a crude extract or purified, if necessary. The anti-fouling compounds of the present invention may be used by formulating the agents in numerous forms including as a paint, a solution and as an emulsion. Formulation is carried out as usual without any difficulties.

For example, when the reagents of the present invention are used as a paint, an anti-fouling paint is prepared by formulating one of the active ingredients described above with other components as described below. The anti-fouling paint can then be applied to ship hulls, underwater structures and inlet channels of water cooling systems. The anti-fouling paint comprises the active ingredient of the present invention and film-forming ingredients including solvents which are selected according to use, extender pigments, coloring pigments and additives. Film-forming ingredients includes chlorinated rubber resin, vinyl acetate resin, acrylic resin and natural resin. The active ingredient is typically formulated 1–45% by weight based on the weight of the anti-fouling paint, preferably 5–20%.

When the reagents of the present invention are used as a solution, an anti-fouling solution is prepared by formulating the active ingredients with film-forming ingredients as described above and by dissolving the mixture in solvents.

The anti-fouling solution is then applied to farming nets and set-nets in order to prevent overgrowth of the fouling organisms. Film-forming ingredients used in the anti-fouling solution include chlorinated rubber resin, vinyl acetate resin, acrylic resin and natural resin. Solvents include toluene, xylene, cumene, methylisobutylketon, ethyl acetate and methanol. Additives such as a plasticizer can be added to the anti-fouling solution, if necessary. The active ingredient is typically formulated 2–70% by weight based on the weight of an anti-fouling solution, preferably 5–30%.

When the agent is employed as a emulsion, an anti-fouling solution is prepared according to the conventional method in the art, by dissolving active ingredients described above in solvents and by adding surfactants to the mixture. Surfactants include those typically used in the art. When the agents of the present invention are used as emulsion, the active ingredient is typically formulated 5–50% by weight based on the weight of the anti-fouling emulsion, preferably 10–40%. The anti-fouling reagents of the present invention may be used by L>5 kneading the agents into the polymer resin materials of fishing nets and the materials of underwater structure such as concrete.

EXAMPLES

The present invention will be more readily understood with reference to the following examples. However, these examples are intended to illustrate the present invention and are not to be construed to limit the scope of the invention.

EXAMPLE 1

Effect of indole compounds in Table 1, on Balanus and Artemia

Various indole compounds were tested for their affect on the attachment of the larvae of *Balanus amphitrite*, an infamous fouling organism, as well as their affect on other beneficial organisms such as *Artemia salina*, a zooplankton used as feed for juvenile fish.

Selected compounds in Table 1, 0.05 mg each, were dissolved in 0.1 ml methanol. Round plates (4 cm in diameter) were then uniformly coated with the solution and air-dried to evaporate methanol. 5 ml of filtered sea water, 10 larvae of *B. amphitrite* in the attachment stage of the development, and 5 larvae of *A. salina* were placed in each plate. The plate was incubated in the darkroom at 23° C. for 24 hours. After 24-hour incubation, the number of molted *B. amphitrite* attached to the bottom of the plate was counted to evaluate the effect of the test compound and the number of dead. *A. salina* was also counted to evaluate the safety of the compound for beneficial organism.

As comparison, a similar test was carried out using 0.05 mg of Bis(tributyltin)oxide (hereafter referred to as "TBTO") instead of the compound in Table 1.

The above test was repeated three times and the resulting numbers were averaged. Table 2 shows the results. The compound number in Table 2 corresponds the compound numbers used in Table 1.

TABLE 2 (%)

| Compound No. | Attachment Rate of larvae | Mortality of Artemia |
|---|---|---|
| 2 | 0 | 0 |
| 4 | 0 | 0 |
| 6 | 0 | 0 |
| 8 | 0 | 0 |
| 10 | 5 | 0 |
| 12 | 5 | 0 |
| 14 | 10 | 0 |
| 16 | 10 | 0 |
| 18 | 15 | 0 |
| 20 | 0 | 0 |
| 22 | 0 | 0 |
| 24 | 0 | 0 |
| 26 | 0 | 0 |
| 28 | 0 | 0 |
| 30 | 0 | 0 |
| 32 | 0 | 0 |
| 34 | 0 | 0 |
| 36 | 0 | 0 |
| 38 | 0 | 0 |
| 40 | 0 | 0 |
| 42 | 0 | 0 |
| 44 | 5 | 0 |
| 46 | 10 | 0 |
| 48 | 10 | 0 |
| 50 | 0 | 0 |
| 52 | 15 | 0 |
| 54 | 0 | 0 |
| 56 | 0 | 0 |
| 58 | 0 | 0 |
| 60 | 0 | 0 |
| 62 | 15 | 0 |
| 64 | 0 | 0 |
| 66 | 0 | 0 |
| 68 | 10 | 0 |
| TBTO | 0 | 100 |
| non-agent | 85 | 0 |

EXAMPLE 2

Comparison of the anti-fouling reagents of the invention with Copper Sulfate and TBTO Various indole compounds of formula (1) wherein $X^2$ is the di-lower-alkylamino-lower alkyl, were tested for their affect on the attachment of larvae of *B. amphitrite*.

Selected compounds in Table 1, 0.05 mg and 0.005 mg each, were dissolved in 0.1 ml methanol. Round plates (4 cm in diameter) were then uniformly coated with the solution and air-dried for removing methanol. 5 ml of filtered sea water, 10 larvae of *B. amphitrite* in the attachment state of the development were placed in each plate. The plate was incubated in the darkroom at 23° C. for 24 hours. After 24-hour incubation, the number of molted *B. amphitrite* attached to the bottom of the plate was counted to evaluate the effect of the test compound.

As a comparison, a similar test was carried out using Copper Sulfate and TBTO instead of the compound in Table 1. The above test was repeated three times and the resulting numbers were averaged. Table 3 shows the results. The compound number in Table 3 corresponds the number used of Table 1.

TABLE 3

| Compound No. | Dosage (mg/5 ml) and attachment rate of larvae (%) | | Condition of non-attached larvae |
|---|---|---|---|
| | 0.05 mg | 0.005 mg | 0.05 mg-dosage |
| 70 | 0 | 35 | vigorously swim |
| 71 | 0 | 15 | vigorously swim |

TABLE 3-continued

| Compound No. | Dosage (mg/5 ml) and attachment rate of larvae (%) | | Condition of non-attached larvae |
|---|---|---|---|
| | 0.05 mg | 0.005 mg | 0.05 mg-dosage |
| 72 | 0 | 0 | vigorously swim |
| 73 | 0 | 5 | vigorously swim |
| 74 | 0 | 5 | vigorously swim |
| 75 | 0 | 5 | vigorously swim |
| 76 | 0 | 0 | vigorously swim |
| 77 | 0 | 0 | vigorously swim |
| 78 | 0 | 0 | vigorously swim |
| 79 | 0 | 0 | vigorously swim |
| 80 | 0 | 5 | vigorously swim |
| 81 | 0 | 0 | vigorously swim |
| 82 | 0 | 0 | vigorously swim |
| 83 | 0 | 0 | vigorously swim |
| 84 | 0 | 10 | vigorously swim |
| 85 | 0 | 0 | vigorously swim |
| 86 | 0 | 0 | vigorously swim |
| 87 | 0 | 0 | vigorously swim |
| 88 | 0 | 0 | vigorously swim |
| 89 | 0 | 0 | vigorously swim |
| 90 | 0 | 5 | vigorously swim |
| 92 | 0 | 25 | vigorously swim |
| 93 | 0 | 35 | vigorously swim |
| Copper Sulfate | 0 | 30 | all larvae died |
| TBTO | 0 | 0 | all larvae died |
| Non-agent | 85 | | |

As is evident from Table 3, Copper Sulfate and TBTO prevent *Balanus* from attachment based on their toxicities, otherwise the reagents of the present invention prevent the organisms from attaching without killing them.

EXAMPLE 3

Compound No. 91 obtained from Zoobotryon pellucidum 2.1 Kg of *Zoobotryon pellucidum* (*phylum Tentaculata, class Bryozoan*) were extracted with 3 Kg of acetone. After extraction, acetone was removed under reduced pressure and the residue was partitioned with 800 ml ethyl acetate and 1200 ml water. The ethyl acetate layer was separated and evaporated under reduced pressure. The resulting residue was purified by silica gel chromatography using an eluent of 30% ethyl acetate in hexane (v/v) to give 610 mg of Compound No. 91.

In the analyses, $^1$H-NMR spectrum, visible light absorption spectrometry, and mass spectrometry, the compound thus obtained was found to be equivalent to the compound in the art.

EXAMPLE 4

Comparison of the anti-fouling effect of Compound No. 91 with Copper Sulfate and TBTO Compound No. 91 obtained in Example 3 was tested for effect on attachment using the larvae of *B. amphitrite*.

0.05 mg of Compound No. 91 was dissolved in 0.1 ml methanol. Round plates (4 cm in diameter) were then uniformly coated with the solution and air-dried to remove methanol. 5 ml of filtrated sea water, 10 larvae of *B. amphitrite* in the attachment stage of the development were placed in each plate. The plate was incubated in the darkroom at 23° C. for 24 hours. After 24-hour incubation, the number of molted *B. amphitrite* attached to the bottom of the plate was counted to evaluate the effect of the test compound. As a comparison, a similar test was carried out using 0.1 mg of Copper Sulfate, 0.05 mg of TBTo and the absence of any agent instead of Compound No. 91. Table 4 shows the results.

TABLE 4

| Test Plot | Active Ingredient | Dosage (mg) | Attachment rate (%) | Condition of non-attached larvae |
|---|---|---|---|---|
| Example 4 | Compound No. 91 | 0.5 | 0 | Vigorously swim (50%) |
| Comparison 4 Copper Sulfate | | 0.1 | 0 | All larvae died |
| Comparison 5 TBTO | | 0.05 | 0 | All larvae died |
| Comparison 6 Non-agent | | 0 | 70 | Vigorously swim (100%) |

EXAMPLE 5

Formulation of the anti-fouling reagents of the invention

When the anti-fouling reagents of the present invention is used as a preventive paint for the attachment of fouling organisms, the formulation is as follows:

| Formulation 1 | |
|---|---|
| Composition | Weight (%) |
| Invention compound | 15 |
| Rosin WW | 6 |
| VYHH (synthetic vinyl resin) | 6 |
| Tricresyl phosphate | 2 |
| Talc | 15 |
| Barium sulfate | 15 |
| Red iron oxide | 10 |
| Xylene | 26 |
| Methylisobutylketone | 5 |
| Total | 100 |

| Formulation 2 | |
|---|---|
| Composition | Weight (%) |
| Invention compound | 10 |
| Rosin WW | 6 |
| VYHH (synthetic vinyl resin) | 6 |
| Tricresyl phosphate | 2 |
| Talc | 20 |
| Barium sulfate | 15 |
| Red iron oxide | 10 |
| Xylene | 20 |
| Methylisobutylketone | 11 |
| Total | 100 |

What is claimed is:

1. A method for preventing the attachment of underwater fouling organisms on a surface comprising:
   treating the surface with an underwater anti-fouling composition comprising at least one indole compound represented by the Formula (1):

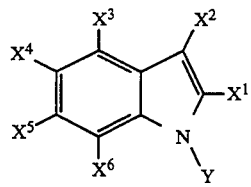

wherein Y is selected from the group consisting of hydrogen, lower alkyl and phenyl; and wherein $X^1$, $X^2$, $X^3$, $X^4$, $X^5$ and $X^6$ are independently selected from the group consisting of hydrogen, halogen, lower alkyl, lower alkoxy, nitro, cyano, cyano lower alkyl, halogenated lower alkyl, substituted or unsubstituted phenyl, aralkyl, aralkyloxy, lower alkoxycarbonyl, aliphatic lower acyl, aliphatic lower acyloxy, lower alkoxycarbonyl-lower alkyl, aromatic acyl, lower-cycloalkylamino-lower alkyl, nitrovinyl, pyridyl lower alkyl, carbamoyl lower alkyl, carbamoyl, diallylamino lower alkyl and di-lower-alkylamino-lower alkyl.

2. The method of claim 1 wherein the underwater anti-fouling composition is a paint.

3. The method of claim 2 wherein the underwater anti-fouling composition further comprises a film-forming ingredient.

4. The method of claim 3 wherein the film-forming ingredient is selected from the group consisting of chlorinated rubber resin, vinyl acetate resin, acrylic resin and natural resin.

5. The method of claim 4 wherein the anti-fouling paint comprises about 1–45% by weight of the indole.

6. The method of claim 3 wherein the anti-fouling composition comprises about 2–70% by weight of the indole.

7. The method of claim 1 wherein the underwater anti-fouling composition is an emulsion.

8. The method of claim 7 wherein the composition further comprises a surfactant.

9. The method of claim 8 wherein the emulsion comprises about 5–50% by weight of the indole.

* * * * *